(12) United States Patent
Velasquez

(10) Patent No.: US 10,758,412 B2
(45) Date of Patent: Sep. 1, 2020

(54) ONE PIECE FLAT DEVICE OF FOR THE DRAINAGE OF AQUEOUS HUMOR FROM THE EYE

(71) Applicant: Mario Eduardo Miranda Velasquez, Lima (PE)

(72) Inventor: Mario Eduardo Miranda Velasquez, Lima (PE)

(*) Notice: Subject to any disclaimer, the term of this patent is extended or adjusted under 35 U.S.C. 154(b) by 68 days.

(21) Appl. No.: 15/378,946

(22) Filed: Dec. 14, 2016

(65) Prior Publication Data

US 2017/0095370 A1   Apr. 6, 2017

Related U.S. Application Data

(63) Continuation-in-part of application No. PCT/EP2015/000009, filed on Jul. 1, 2015.

(30) Foreign Application Priority Data

Jul. 1, 2015 (PE) .................... 001057-2014/DIN

(51) Int. Cl.
*A61F 9/007* (2006.01)

(52) U.S. Cl.
CPC .. *A61F 9/00781* (2013.01); *A61F 2230/0019* (2013.01)

(58) Field of Classification Search
CPC ............... A61F 9/00781; A61F 2230/0019
See application file for complete search history.

(56) References Cited

U.S. PATENT DOCUMENTS

| 5,601,094 | A | 2/1997 | Reuss |
| 5,704,907 | A | 1/1998 | Nordquist et al. |
| 7,207,965 | B2 | 4/2007 | Simon |
| 2006/0155238 | A1 | 7/2006 | Shields |
| 2011/0105986 | A1* | 5/2011 | Bronstein ............ A61F 9/0017 604/8 |
| 2013/0150770 | A1 | 6/2013 | Horvath et al. |

FOREIGN PATENT DOCUMENTS

WO    WO2004/056294    *    7/2004

OTHER PUBLICATIONS

International Search Report for related PCT application PCT/PE2015/000009 and translation.
Peruvian Search Report for 001057-2014/DIN, dated Jul. 1, 2014.

* cited by examiner

*Primary Examiner* — Ariana Zimbouski
(74) *Attorney, Agent, or Firm* — Husch Blackwell LLP

(57) ABSTRACT

The invention relates to a stainless steel device for permanent insertion into the sclerocorneal limbus, with different drainage and anchorage systems, enabling the aqueous humour to discharge through one or more virtual spaces from the anterior chamber to an intrascleral space in cases of simple glaucoma or to the equatorial episclera in cases of complex glaucoma, such as neovascular glaucoma. The space is virtual, not real, as in the case of the tubular device. It enables the aqueous humour to discharge slowly and continuously, minimizing the possibility of the chamber being flat or of germs penetrating through the device. Furthermore, the anchorage system is less aggressive, thus reducing the possibility of bleeding.

7 Claims, 7 Drawing Sheets

ONE PIECE FLAT DEVICE OF FOR THE DRAINAGE OF AQUEOUS HUMOR FROM THE EYE

This is a continuation-in-part of International Application PCT/PE2015/000009, with an international filing date of Jul. 1, 2015.

TECHNICAL FIELD

The present invention relates to the field of ophthalmic ocular implants, and refers to an intraocular implant device for permanent insertion in the corneal limbus that allows the formation of a new drainage point.

BACKGROUND OF THE INVENTION

Glaucoma is, after diabetes, the second leading cause of blindness in the world. Vision loss as a result of glaucoma involves both central and peripheral vision and has a major impact on the ability of people to live independent lives.

Glaucoma is an eye disease caused by an elevated pressure within the eyeball, which damages the optic nerve and eventually produces total and irreversible loss of sight. It is produced by a failure in the natural drainage system of the eye, resulting in a reduced capacity for draining aqueous humor, which is a fluid that is produced continuously inside the eye as part of its normal functioning. As a result of this failure in the natural drainage system, fluid outflow is reduced and therefore the pressure within the eyeball is increased.

The Glaucoma is an optic neuropathy (a disorder of the optic nerve) caused by an elevated intraocular pressure. The high pressure inside the eye compresses the outlet of the optic nerve (papilla) causing changes in its appearance and in the visual function (increase of the optic cup and alterations to the visual field). If the pressure remains increased over a prolonged period of time, a complete and irreversible vision loss takes place.

The intraocular pressure is maintained by a balance between the production and the outflow of aqueous humor. Aqueous humor is a fluid produced by the ciliary body in the posterior chamber of the eye at a rate of approximately 3 to 5 microliters per minute. The fluid produced then passes through the pupillary opening of the iris into the anterior chamber of the eye. Once in the anterior chamber, the fluid leaves the eye through the junction between the cornea and the iris (iridocorneal angle) through a filter called Trabecula, which is composed by collagen bundles arranged in three-dimensional structure similar to a sieve. From that point the aqueous humor goes to the Schlemm's canal and then to the episcleral veins.

As the eye is a closed and inelastic sphere, the production and outflow of aqueous humor necessarily have to be equal. This causes a pressure inside the eye that is determined by the amount of fluid produced and the capacity of outflow that it has. In normal conditions, the intraocular pressure ranges between 10 and 21 mm Hg.

If the production of aqueous humor increases, the intraocular pressure will increase to achieve greater outflow. If the outflow resistance increases, the intraocular pressure will increase to increment the outflow. Both scenarios will increase intraocular pressure and may cause glaucoma, being much more frequent the increase in the outflow resistance.

The resistance to the outflow of aqueous humor may be increased by several factors. Thus, in the "primary open angle glaucoma (POAG)" (responsible for 85% of glaucoma), the abnormal resistance is produced along the outer aspect of the trabecular meshwork and the inner wall of the Schlemm's canal. In the "primary angle closure glaucoma (PACG)" the resistance increases by mechanical blocking of the angle and in "secondary glaucoma" due to diverse motives such as inflammatory waste deposits, vascularization of the area, pigment blocking, etc.

Whatever the factor that produces it, increased intraocular pressure compresses the outlet of the optic nerve and interferes in its vascularization, causing the death of nerve cells that carry the visual stimulus to the brain, producing alterations in the visual field and, in advanced cases, total and irreversible blindness.

The only therapeutic approach currently available for glaucoma is to lower intraocular pressure.

The clinical treatment of glaucoma is done step by step, the first step being the medical treatment either by oral means or with drops.

The drugs work by reducing aqueous humor production or by facilitating its outflow. The drugs that are currently available can have many side effects, some serious that include congestive heart failure, respiratory distress, hypertension, depression, kidney stones, aplastic anemia, sexual dysfunction and death. Compliance with medication is also a major problem, being estimated that more than half of glaucoma patients do not follow their dosing schedules correctly.

While medications work, they will be the recommended treatment, but often are not sufficient to maintain a safe intraocular pressure and surgery is needed. The most frequent surgeries are Trabeculoplasty and Trabeculectomy.

In laser trabeculoplasty, thermal energy from a laser is applied to a number of noncontiguous spots in the trabecular meshwork. It is believed that the laser energy somehow stimulates the metabolism of the trabecular cells and changes the extracellular material of the trabecular meshwork. In approximately 80% of patients, aqueous outflow is increased and the pressure decreases. However, the effect often is not long lasting and 50% of patients develop hypertension again in five years.

In addition, laser trabeculoplasty is not an effective treatment for primary open angle glaucoma (POAG) in patients of less than fifty years old nor is effective for glaucoma due to angle closure and many secondary glaucomas.

If laser trabeculoplasty does not reduce the pressure to the desired level, filtering surgery is then performed.

The most commonly used filtering procedure is the trabeculectomy. In a trabeculectomy an incision is made in the conjunctiva, which is the transparent tissue that covers the sclera. The conjunctival tissue is lifted and a scleral flap of approximately 4×4 mm is made with a depth of 50% of the scleral thickness and is lamellar dissected up to 1 mm into the cornea. The anterior chamber is entered beneath the scleral flap and a section of the deep sclera and trabecular meshwork is excised. The scleral flap is loosely sewn back into place and conjunctival incision is closed well. Postoperatively, the aqueous humor passes through the hole beneath the scleral flap and goes to the sub conjunctival space where it forms a blister from where it passes to the blood vessels of the conjunctiva or traverses the conjunctiva to the surface.

Trabeculectomy is associated with many problems, among them, the fibroblasts that are present in the episclera proliferate, migrate and can scar the scleral flap, failures in scarring may occur, particularly in children and young adults. Of the eyes that have had an initially successful trabeculectomy, 80% will stop filtering in a period of 3 to 5 years after surgery. To minimize fibrosis, surgeons are now are applying antifibrotic agents such as mitomycin C (MMC) and 5-fluorouracil (5-FU) to the scleral flap at the time of surgery. The use of these agents has increased the success rate of trabeculectomy, but also has increased its complications.

When trabeculectomy does not successfully lower the eye pressure, the next surgical step is often an aqueous shunt valve. This device consists of a silicone tube that is attached at one end to a plastic plaque (polypropylene or other synthetic) with valve shape that is sewn to the ocular equator or a tittle after this point and the other end of the silicone tube is introduced into the anterior chamber through a hole made in the corneal limbus. The outer portion of the tube is covered with sclera or pericardium from donor, it is all covered with the conjunctiva and the incision is closed. There are many problems with the current technology of these aqueous shunt valves, including bad scarring, valve failure, hypotony and infection.

In the year 1999 the company Optonol patented a tubular filtering device, not valved for the control of intraocular pressure in glaucoma (Patent U.S. Pat. No. 5,968,058). This device was a small stainless steel tube that, once placed in the corneal limbus, allowed the flow of aqueous humor through the tube from the anterior chamber to an intrascleral space and from there to the sub conjunctival space. Since 2002, the company Alcon sells this device under the name of Ex-Press.

The implantation of these permits less invasive surgeries compared to the trabeculectomy, because allows the aqueous humor outflow without the need of extracting a segment of the trabecula or performing an iridectomy.

Several studies have reported on the effectiveness of these devices to significantly reduce intraocular pressure, but also report of complications, been the most common frequent flat chamber (excessive loss of eye pressure) and bleeding in anterior chamber, which is believed may be related with the anchoring system.

All the surgical techniques to reduce intraocular pressure seek to create a new drainage pathway for aqueous humor that can replace the obstructed normal path, with the fewest amount of possible complications.

However, the current treatments and surgical techniques may present complications such as:
  May get obstructed or stop functioning in a short period of time.
  May produce an excessive loss of pressure in the eye.
  May produce intraocular bleeding and associated complications.
  May produce infections.
  May require complex and aggressive surgery.

In this sense, the flat drainage device for the control of intraocular pressure in glaucoma presented in this document has significant advantages over existing alternatives for the surgical treatment of this illness.

DESCRIPTION OF THE INVENTION

The present invention consists is an ocular device to produce a new drainage point, consisting of a flat sheet of stainless steel or other materials that does not adhere to the eye tissues. This characteristic of the material is very important, because non-adherence to ocular tissues is essential for the device to achieve the relief of excessive pressure in a suitable manner.

The device is made of one single piece, and presents three clearly defined parts:
  a first part (A), that it is located in the anterior chamber and due to its shape serves as an anchor;
  a second part (B), which punctures the corneal limbus and connects the anterior chamber with the exterior of the eye; and
  a third part (C), which stays outside the eye in an intra-scleral space, episcleral space or in both.

In medicine, these spaces (intrascleral and episcleral) are considered as the exterior of the eye. The invention allows the aqueous humor to reach this area, where it is absorbed by the tissue of the sclera, which is the white part of the eyeball.

The device functions using physical principles like the search for balance between the forces and pressures that occur inside and outside of the eye. Once placed in the corneal limbus, when the pressure of the eye is increased, the device allows the aqueous humor that is under pressure within the anterior chamber to overcome the resistance produced by the ocular tissue that surrounds parts (B) and (C), creating a space that permits the escape of the liquid, lowering the eye pressure. This is possible because the material that the device is composed of does not adhere to the eye tissues.

When the flow is released and the pressure has been reduced to an adequate level, the forces between the interior and the exterior of the eye are balanced and the connection is temporarily closed, interrupting the flow of aqueous humor.

Then, the device allows a temporary connection that is controlled by the intraocular pressure itself. This way of working is completely different from that of any known device for the treatment of glaucoma, and has the following significant advantages:

1. The way of releasing the aqueous humor achieved by the device is temporary and not permanent, since it depends on the interior pressure of the eye. The temporary release of aqueous humor prevents an excessive loss of ocular pressure from occurring (called flat chamber), because the communication is established only when the pressure increases and is interrupted when it reaches a normal level.

2. In addition, the temporary communication produced by the device prevents infections, because, as it is produced by an increase in the intraocular pressure, outflow of fluid is always in one direction (from the interior to exterior). This reduces significantly the possibility of germs entering from the exterior to the interior of the eye, which is a problem that can occur with devices that allow a permanent connection.

3. The form and the material that the device is made of minimizes the possibility of an obstruction occurring in the space (s) through which the aqueous humor is released and ocular pressure is lowered. This is a serious problem in the existing devices that are made of permeable or filtering materials or those that are hollow tubes or contain tubes, channels or microchannels. They all have a limited section or drainage capacity and are likely to be clogged or obstructed by various factors, such as the natural healing and scaring process of the eye that is produced after the implantation surgeries.

The invented device is a flat and solid sheet, of a material that does not adhere to the eye tissues and that performs the release of aqueous humor through the space that is formed between the material of the device and the ocular tissue that surrounds it and not through the device itself or through the material of which it is composed. Since the section of the space that allows the outflow of fluid that is created by the invented device varies according to the pressure inside the eye, the space can grow bigger to remove any obstruction if this happens. This reduces significantly the possibility of clogging and extends the life expectancy of the device.

4. The invention offers the possibility of reducing a wider range of intraocular pressures than the current devices, because the release of aqueous humor is through the space formed between the device and the eye tissues when the pressure within the eye is increased. Conversely, existing devices perform the drainage through the material that they are composed of or through one of the hollow tubes, channels or microchannels they contain. Those devices have a fixed section and/or dimension and, therefore, a more limited working range or capacity 5. The invention has an anchor system which forms part of the device itself, identified as part (A) in the images, which is different from the ones in known implants. The shape of the tip of the invention makes implantation surgery very fast, easy and non-aggressive, to the point that can be performed by any ocular surgeon with basic instruments. This is especially advantageous in developing countries where glaucoma is a major cause of blindness.

6. The invention is not traumatic to the eye during and after being implanted. The part (A) of the device, which serves as an anchor, has the shape of an inverted pyramid with a rounded lower edge, which makes it non aggressive during the implantation and even facilitates the removal of the device if required. This design detail decreases the possibility of bleeding, which is one of the problems that occur during implantation and/or removal of existing devices.

7. The invention has been implanted and monitored in a group of patients with glaucoma since 2013, obtaining excellent results that confirm the advantages mentioned in points 1 to 6. The invention has been able to reduce the ocular pressure in all the patients in whom it has been implemented and has completely eliminated the pain, which is another of the great suffering of patients with glaucoma. It is important to mention that the results obtained have been in patients with terminal glaucoma who did not respond to any medical or surgical treatment.

The way the device permits the release of the aqueous humor shares the same principle of operation of other systems of the human body. An illustrative example that explains the operation of the device is the way that the vagina controls the release of fluid during menstruation. The vagina is normally closed, but when it receives pressure from the menstrual flow, forms a temporary space of the size needed to let the stream pass and then closes again. Another example is the esophagus, which is normally closed, but when it receives the pressure from the bolus forms a temporary space of the size needed for this to pass and then closes again.

The device is a flat sheet of a material that does not adheres to the eye tissues and that connects the interior with the exterior of the eye. By not adhering to tissues, the surfaces of the device in contact with the eye form a space (s) that allows the outflow of aqueous humor. This space opens and allows the output of aqueous humor only when intraocular pressure increases; and is closed again when this pressure decreases. Then, the drainage is done through what we have called a "temporary space", i.e., a space that is created only when it is necessary. The "temporary space" is created between the device and the ocular tissues surrounding it when the pressure inside the eye increases. It is formed thanks to the shape of the device and the fact that it does not adhere to the eye tissues. The "temporary space" creates an outflow path of one direction through which the aqueous humor will flow at a faster or slower rate depending on the pressure difference between the interior and the exterior of the eye.

The device and the way it drains fluids is applicable to other organs that need drainage from the organ to the exterior and its use is not limited exclusively to the eye.

BRIEF DESCRIPTION OF THE DRAWINGS

The FIG. 1 shows a three-dimensional view of the device of the present invention.

The FIG. 2 shows a side view of the device of the present invention.

Figure 1:
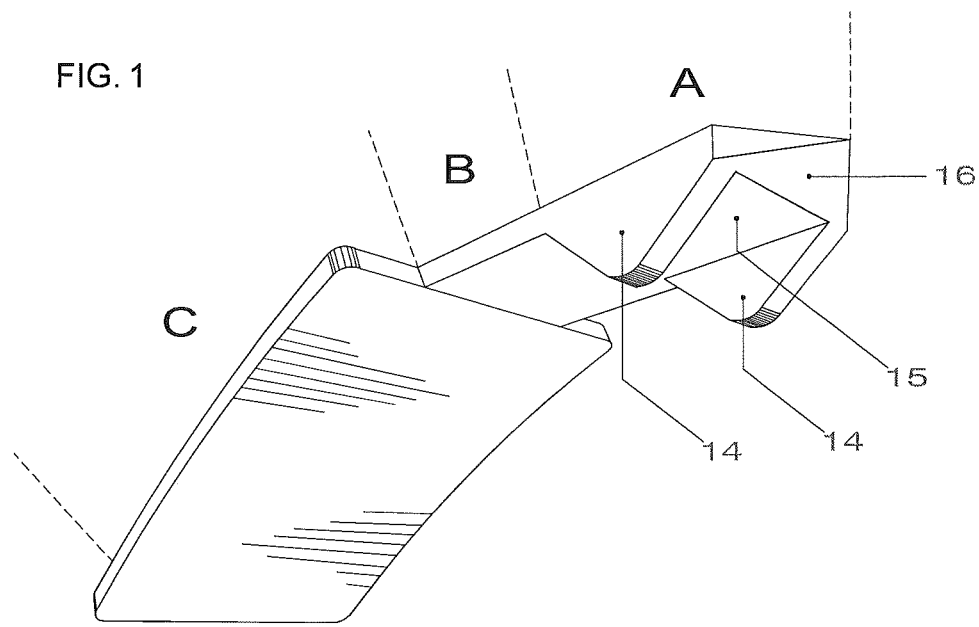
Figure 2:
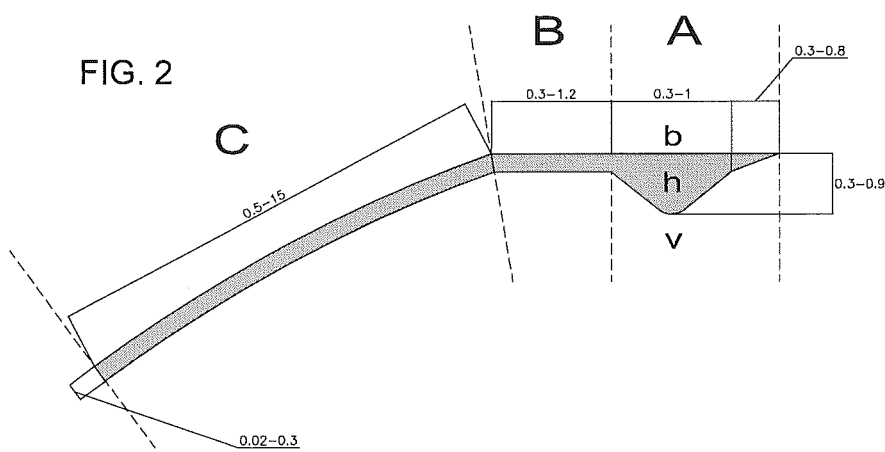
Figure 3:
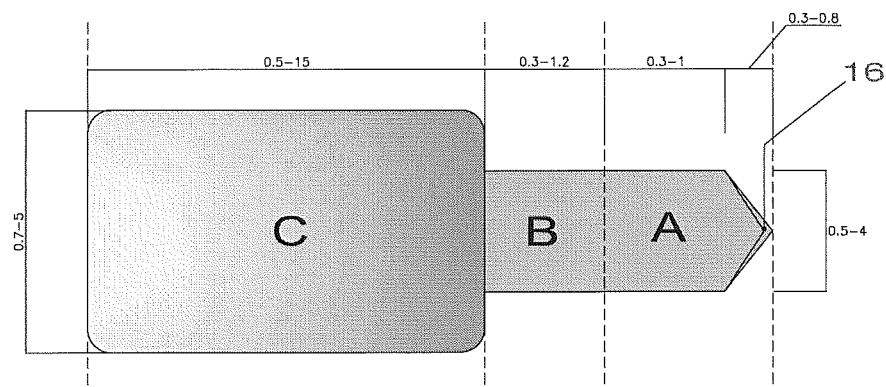

The FIG. 3 shows a top view of the device of the present invention.

Figure 4:
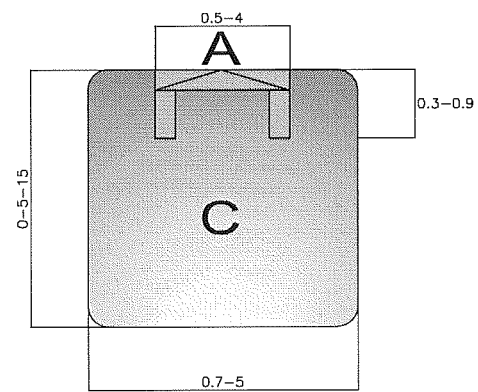

The FIG. 4 shows a front view of the device of the present invention.

Figure 5:
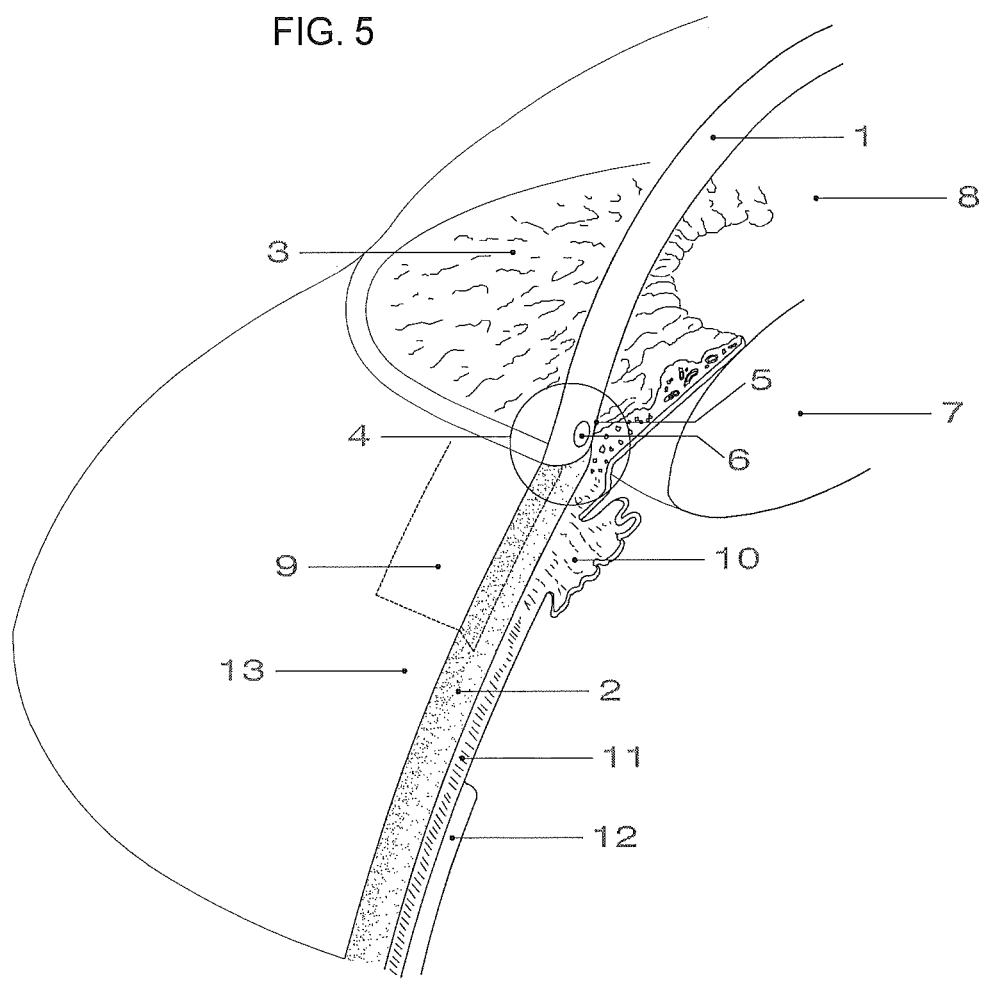

The FIG. 5 shows three-dimensionally a part of the sagittal section of a human eye, where the anatomical details of the iridocorneal angle are shown, which is the area where the present invention will influence. There we can see: Cornea 1, Sclera 2, Iris 3, Corneal Limbus 4, Trabecula 5, Schlemm's Canal 6, Crystalline Lens 7, Anterior Chamber 8, Scleral Flap where the cut will be made for the insertion of the invention 9, Ciliary Body 10, Choroid 11, Retina 12 and Episclera 13.

Figure 6:
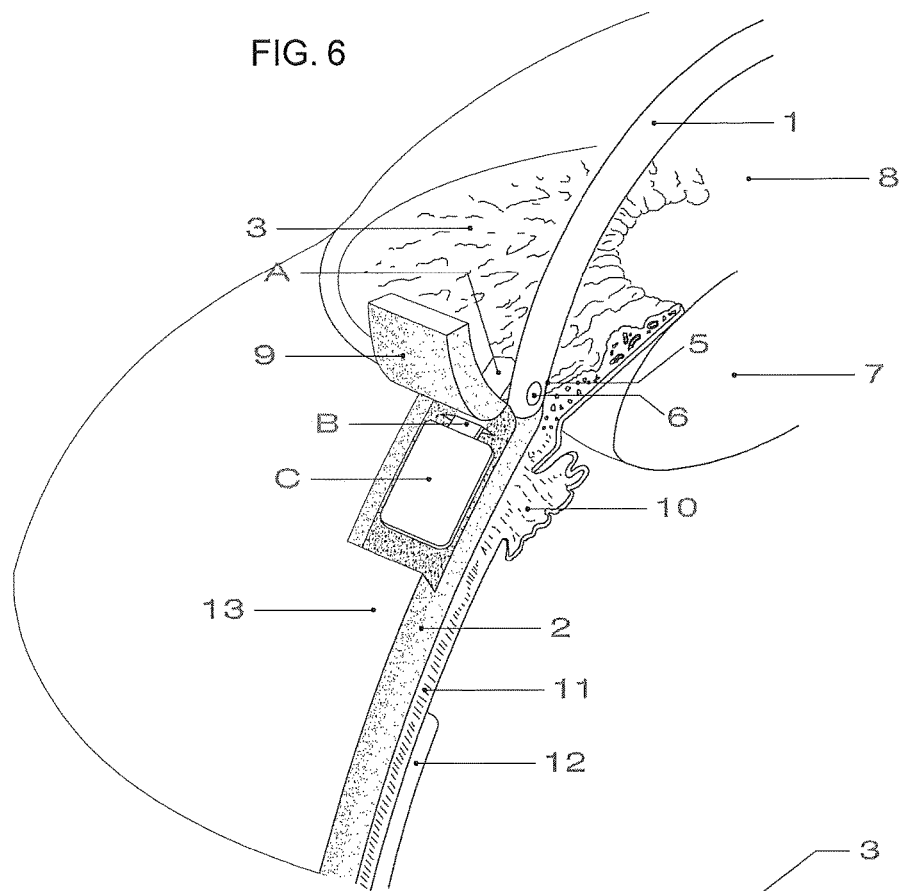

The FIG. 6 shows how the positioning of the device of the present invention is done to its working position and where: The first part (A) is in the anterior chamber 8 and due to its shape of inverted pyramid with rounded lower edge will stabilize the device in its working position and will prevent unintentional detachment. The second part (B) punctures the eye and is in contact, in the area of the perforation, with the cornea 1 on the upper surface of the device and with the sclera 2 on the lower surface of the device. The third part (C) is outside of the eye between the scleral flap 9 and the sclera 2, in contact with the flap 9 on the upper surface and with the sclera 2 on the lower surface. It is through these surfaces of the device, that are in contact with the eye, through which the aqueous humor will flow and be diffused into the intrascleral and sub-conjunctival space.

Figure 7:
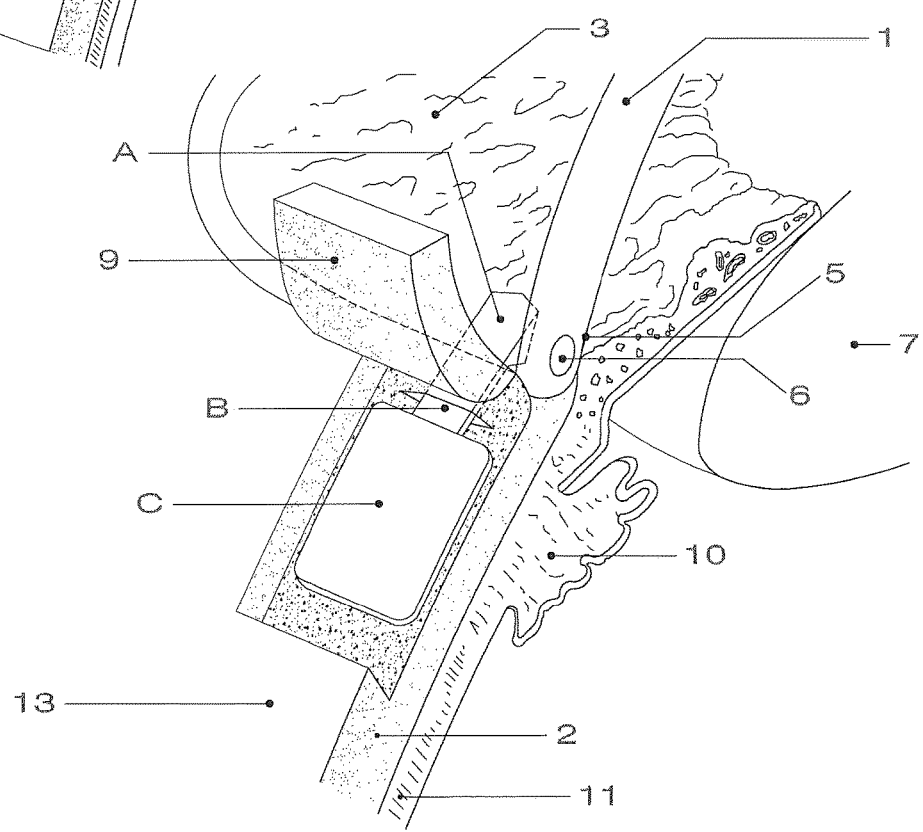

The FIG. 7 shows in detail the area described in FIG. 6, where the device of the present invention is inserted.

Figure 8:
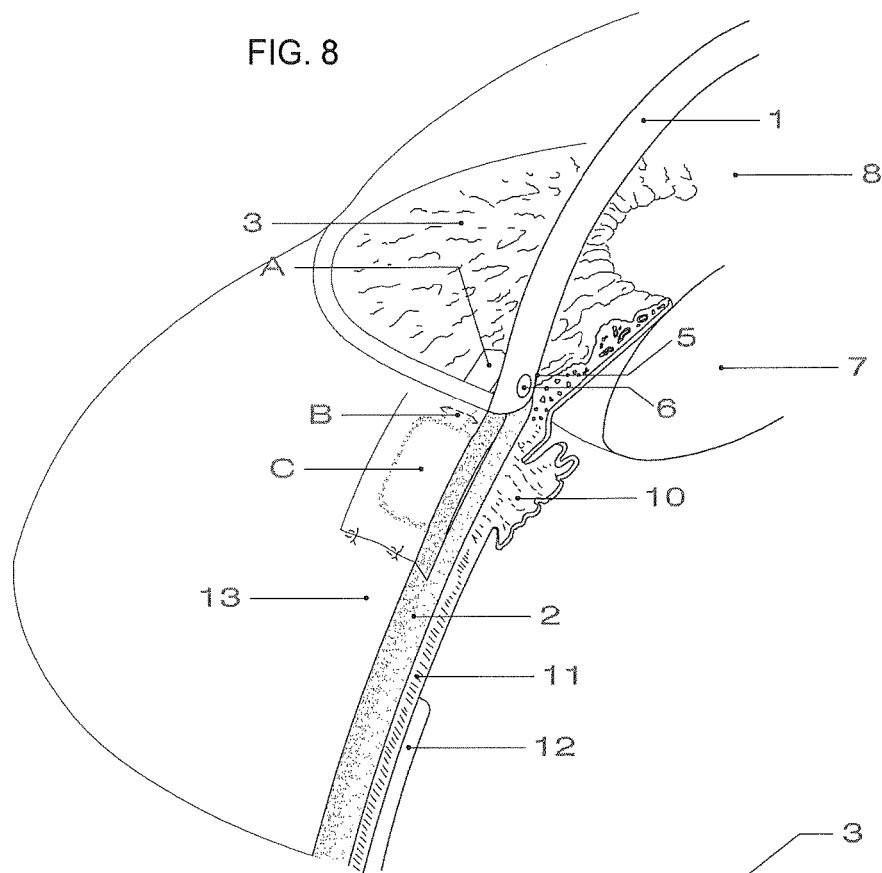

The FIG. 8 shows the device of the present invention in its working position after the insertion procedure is completed and the flap 9 has been returned to its original position and has been sutured. After surgery, the first part (A) is in the anterior chamber 8 and due to its shape of inverted pyramid with rounded lower edge will stabilize the device in its working position and will prevent unintentional detachment. The second part (B) is covered by the sclera and is in contact, in the area of the perforation, with the cornea 1 on the upper surface of the device and with the sclera 2 on the lower surface of the device. The third part (C) is outside of the eye and covered by the scleral flap 9. It is through these surfaces of the device, that are in contact with the eye, through which the aqueous humor will flow and be diffused into the intrascleral and sub-conjunctival space.

Figure 9:
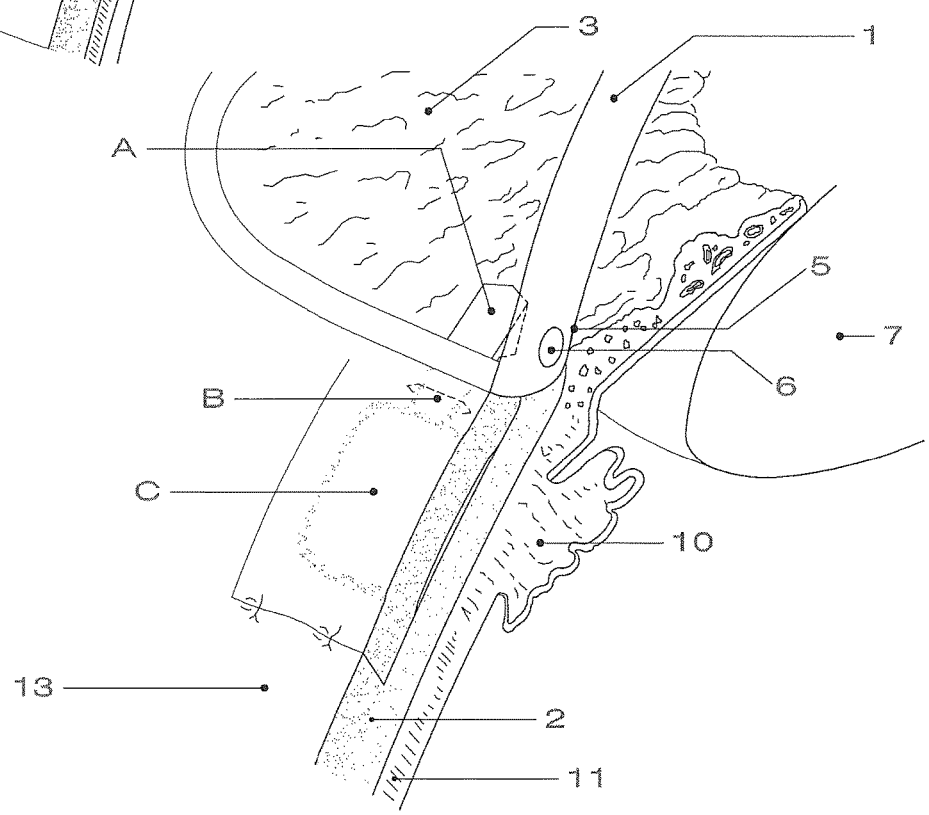

The FIG. 9 is a detailed diagram of the description given in FIG. 8, where you can see the area where the device of the present invention is inserted, after the insertion procedure is completed.

Figure 10:
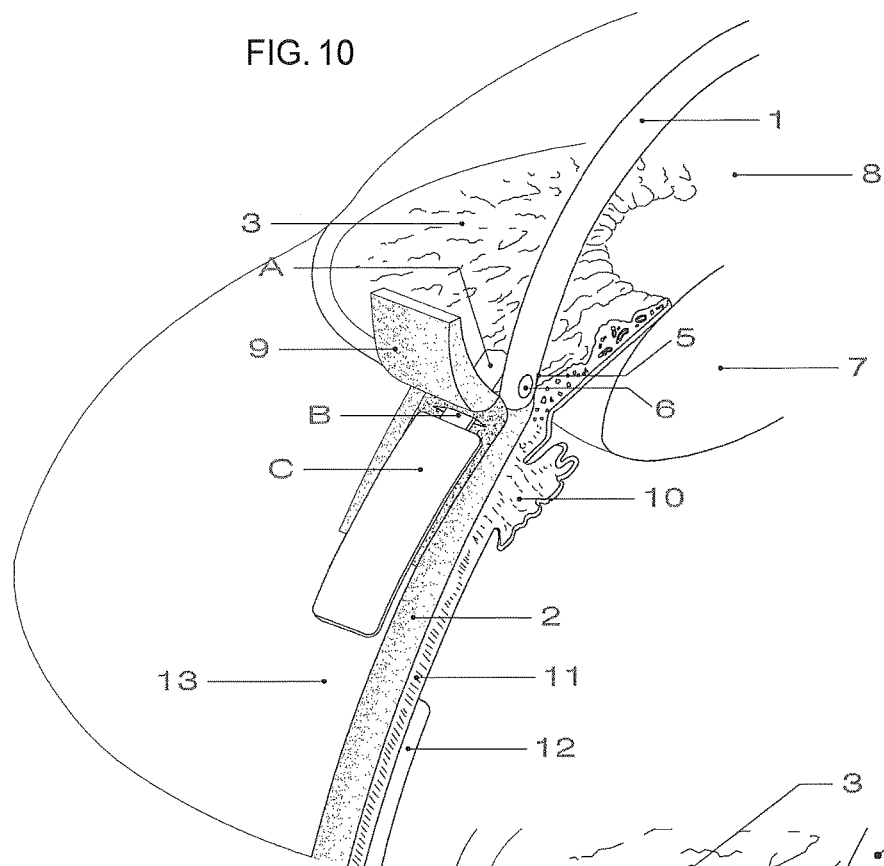

The FIG. 10 shows how is done the positioning to its working position, of a variant of the device of the present invention, where: The first part (A) is in the anterior chamber 8 and due to its shape of inverted pyramid with rounded lower edge 14 will stabilize the device in its working position and will prevent unintentional detachment. The second part (B) punctures the eye and is in contact, in the area of the perforation, with the cornea 1 on the upper surface of the device and with the sclera 2 on the lower surface of the device. The third part (C) is outside of the eye, one part between the scleral flap 9 and the sclera 2, and another part goes out to the episcleral space 13. It is through these surfaces of the device that are in contact with the eye through which the aqueous humor will flow and be diffused into the intrascleral and sub-conjunctival space. This variant of the device creates a longer corridor that leads to the ocular equator, increasing the area of diffusion of the aqueous humor. This can be beneficial in neovascular glaucoma.

Figure 11:
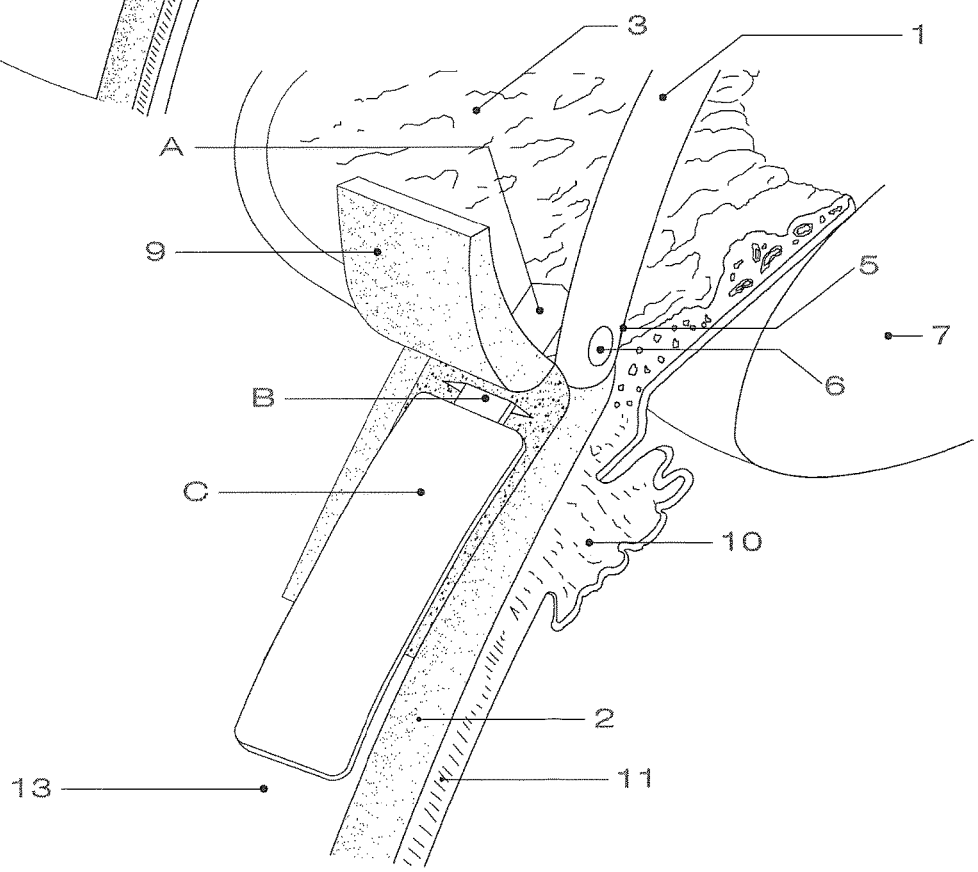

The FIG. 11 is a detailed diagram of the area described in FIG. 10, where the device of the present invention is inserted.

Figure 12:
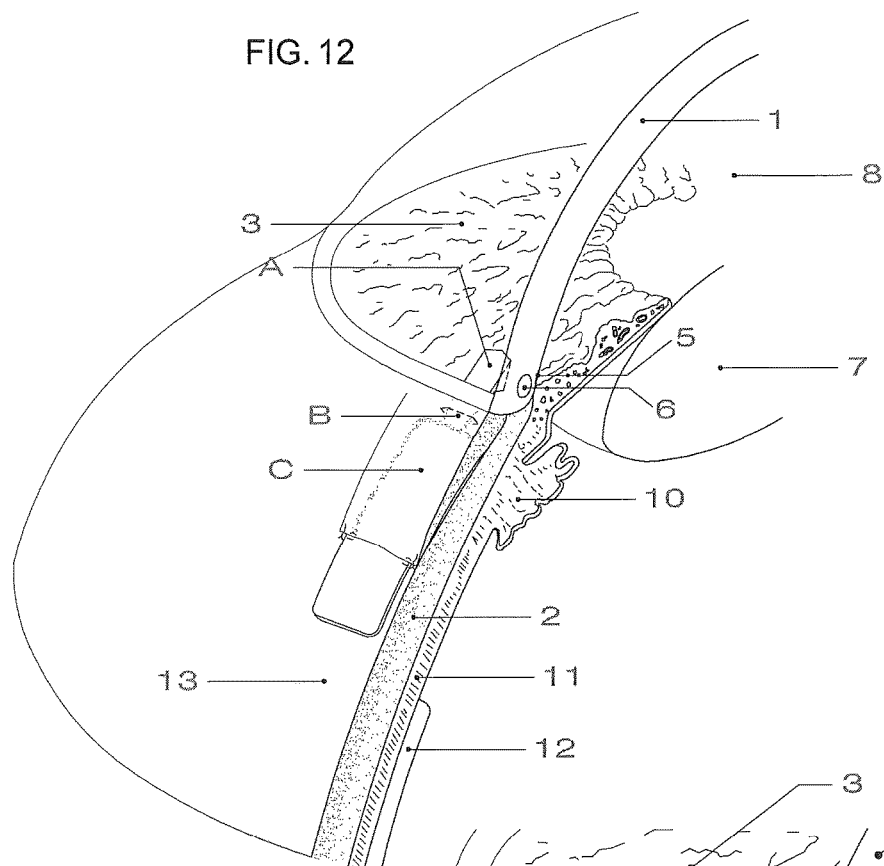

The FIG. 12 shows a variant of the device of the present invention in its working position, after the insertion procedure is completed and the flap 9 has been returned to its original position and has been sutured. After surgery, the first part (A) is in the anterior chamber 8 and due to its shape of inverted pyramid with rounded lower edge 14 will stabilize the device in its working position and will prevent unintentional detachment. The second part (B) is covered by the sclera 2 and is in contact, in the area of the perforation, with the cornea 1 on the upper surface of the device and with the sclera 2 on the lower surface of the device. The third part (C) is outside of the eye, one part between the scleral flap 9 and the sclera 2, and another part goes out to the episcleral space 13. It is through these surfaces of the device that are in contact with the eye, through which the aqueous humor will flow and be diffused into the intrascleral and sub-conjunctival space. This variant of the device creates a longer corridor that leads to the ocular equator, increasing the area of diffusion of the aqueous humor. This can be beneficial in neovascular glaucoma.

Figure 13:
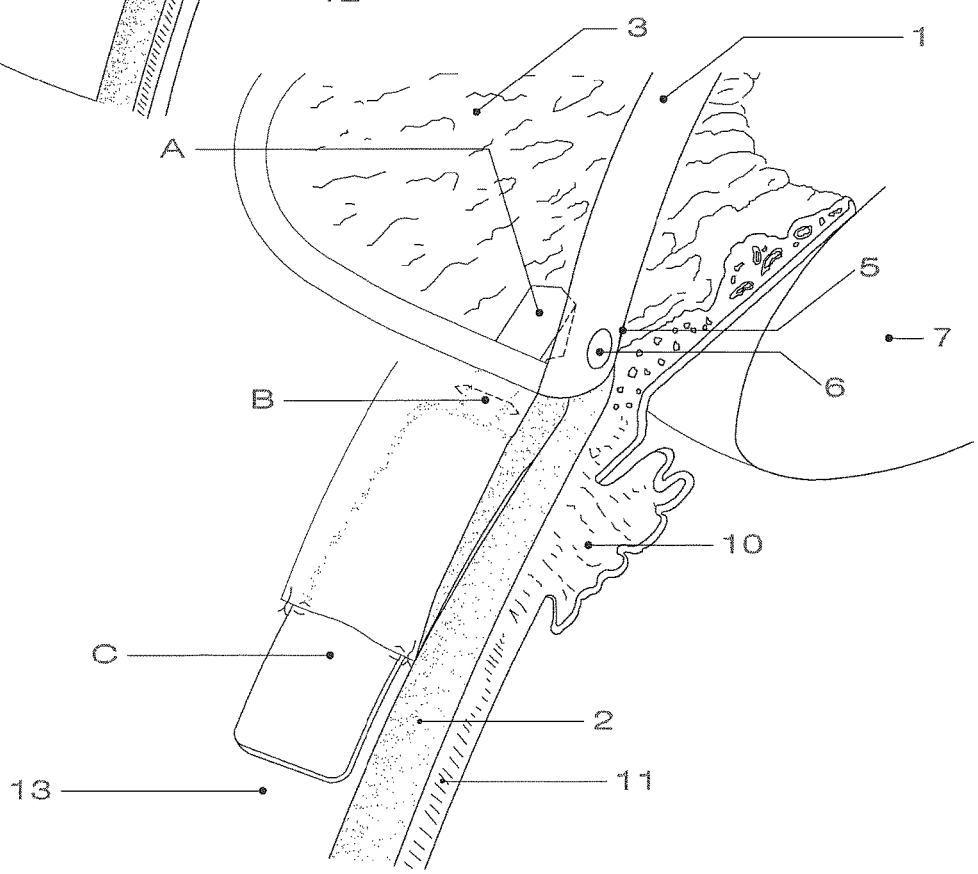

The FIG. 13 is a detailed diagram of the description given in FIG. 12, where you can see the area where the device of the present invention is inserted, after the insertion procedure is completed.

Figure 14:
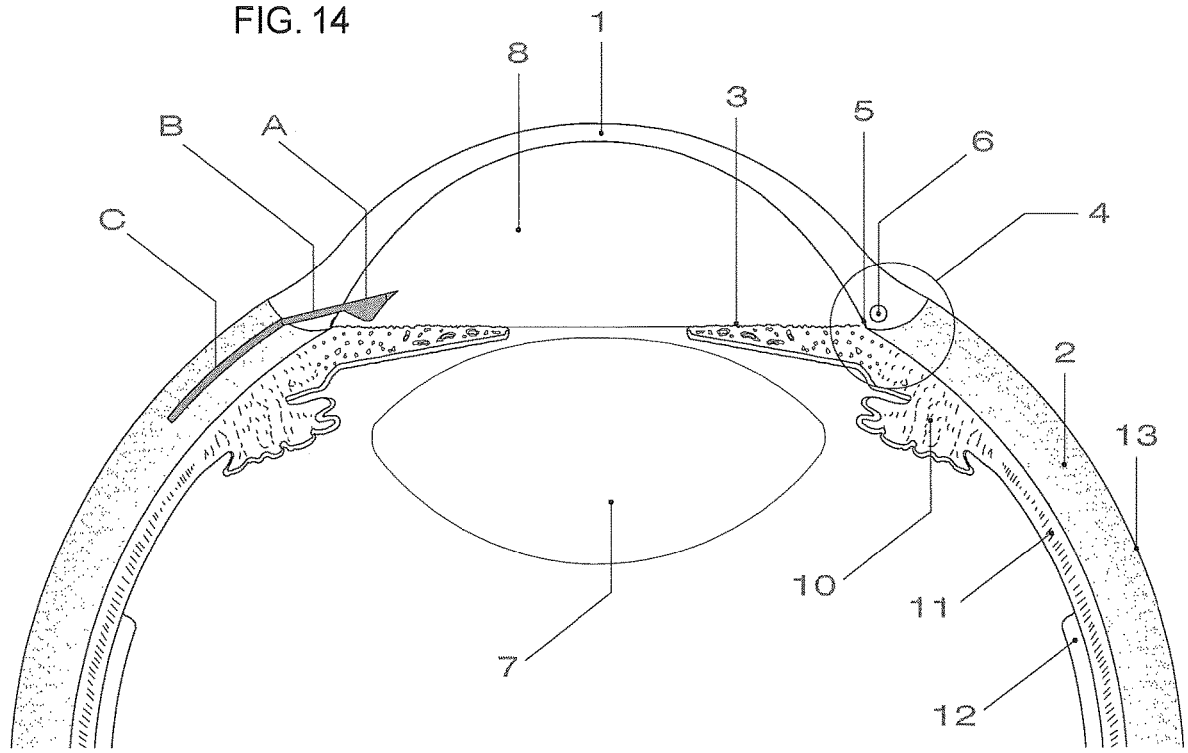

The FIG. 14 shows the sagittal section of a human eye with the device in its working position, where the anatomical details of the iridocorneal angle are shown, which is the area where the present invention will influence. There we can see: Cornea 1, Sclera 2, Iris 3, Corneal Limbus 4, Trabecula 5, Schlemm's Canal 6, Crystalline Lens 7, Anterior Chamber 8, Ciliary Body 10, Choroid 11, Retina 12, Episclera 13. The diagram shows the device of the present invention in its working position. The first part (A) is in the anterior chamber and due to its shape of inverted pyramid with rounded lower edge will stabilize the device in its working position and will prevent unintentional detachment. The second part (B) is covered by the sclera and is in contact, in the area of the perforation, with the cornea on the upper surface of the device and with the sclera on the lower surface of the device. The third part (C) is outside of the eye and covered by the scleral flap. It is through these surfaces of the device that are in contact with the eye, through which the aqueous humor will flow and be diffused into the intrascleral and sub-conjunctival space.

Figure 15:
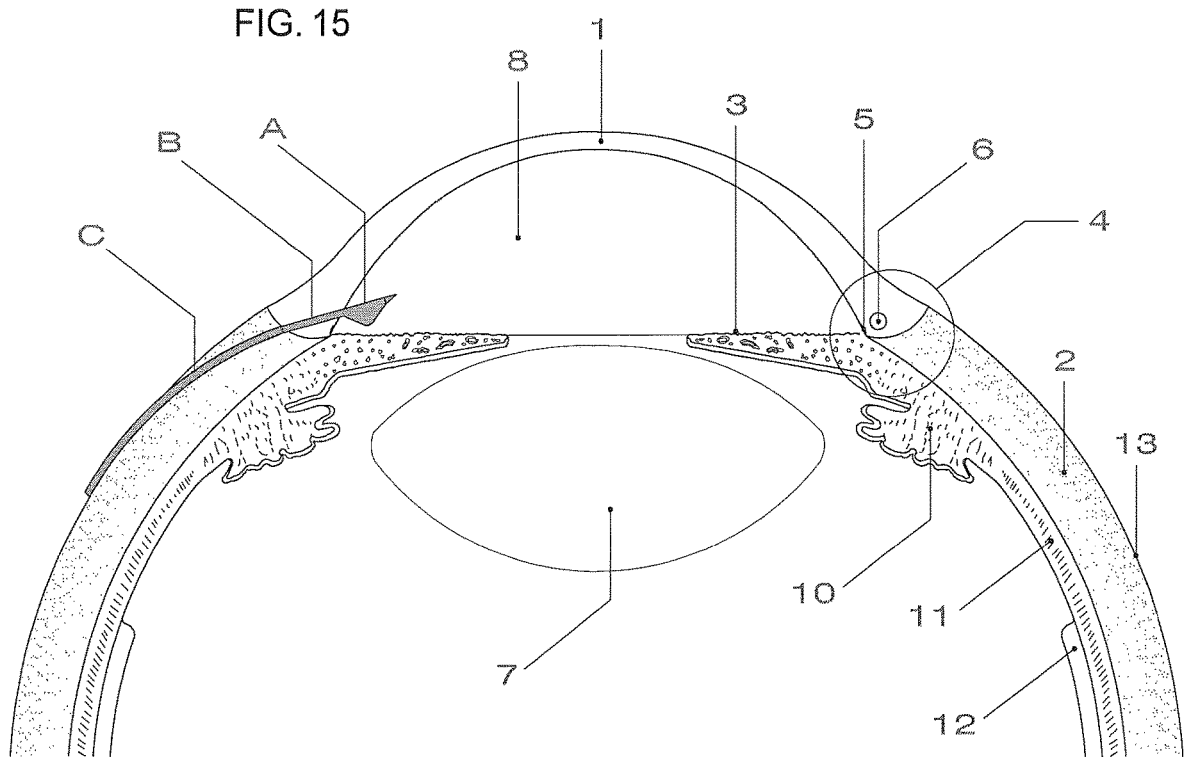

The FIG. 15 shows the sagittal section of a human eye with a variant of the device in its working position, where the anatomical details of the iridocorneal angle are shown, which is the area where the present invention will influence. There we can see: Cornea 1, Sclera 2, Iris 3, Corneal Limbus 4, Trabecula 5, Schlemm's Canal 6, Crystalline Lens 7, Anterior Chamber 8, Ciliary Body 10, Choroid 11, Retina 12, Episclera 13. The first part (A) is in the anterior chamber and due to its shape of inverted pyramid with rounded lower edge will stabilize the device in its working position and will prevent unintentional detachment. The second part (B) punctures the eye and is in contact, in the area of the perforation, with the cornea on the upper surface of the device and with the sclera on the lower surface of the device. The third part (C) is outside of the eye, one part between the scleral flap and the sclera, and another part goes out to the episcleral space. It is through these surfaces of the device that are in contact with the eye through which the aqueous humor will flow and be diffused into the intrascleral and sub-conjunctival space. This variant of the device creates a longer corridor that leads to the ocular equator, increasing the area of diffusion of the aqueous humor. This can be beneficial in neovascular glaucoma.

MODE OF EXECUTION OF THE INVENTION

The present invention consists in an intraocular implant device for permanent insertion in the corneal limbus to regulate the intraocular pressure and control glaucoma. Achieves this purpose through a drainage principle different to any known device.

Since the device is a long term implant, it must be manufactured with a material that is harmless to the tissues and fluids with which it will be in contact. The device must not be absorbed, corroded or structurally compromised during his tenure in situ. In addition, it is equally important that the eye tissues and the aqueous humor do not result adversely affected by the presence of the implanted device.

The device may be made of stainless steel or other biocompatible materials that do not adhere to the eye tissues, among which may be included gold, platinum, silicon, nickel, molybdenum, and other compatible metals, metal alloys, ceramics or polymers or combinations that arise in the future that are within the scope of the present invention.

It is important that the material used does not adhere to the eye tissues in order to create the possibility of generating a "temporary space" that connects the anterior chamber to the exterior of the eye either to an intrascleral space, an episcleral space or to both.

The parts that constitute the invented device are:
Part A:

The part A has at its ends two inverted pyramids 14 joined at their base to a sheet 15. The lower vertex of each of these inverted pyramids 14 is rounded to facilitate the insertion of the device. This will allow the device to have a non-traumatic anchor, facilitating its insertion or removal. The part A will have a sharp region on its forward end 16, to facilitate the insertion of the device, and to the back end will be continued with the Part B.

The part A, which is in the anterior chamber 8, between the cornea 1 and iris 3, has at its ends two inverted pyramids 14 joined to the sheet 15 by their upper base b, of measures between 0.3 and 1 mm. Each inverted pyramid will have a height h between 0.3 and 0.9 mm and a rounded lower vertex v to facilitate the insertion and removal of the device. This will allow a non-traumatic anchor. As shown in the diagram, the device has an angle between part B and part C, designed to follow the natural curvature of the eye, which can be variable.

The part A has the form of a rectangular sheet 15 of which emerge, towards the bottom part, two inverted pyramids 14. This sheet, on the proximal side is continued by part B, and on the distal side becomes a sharp triangle 16 to facilitate the insertion of the device. The rectangular sheet has a width equal to that of the portion B, between 0.5 and 4 mm, and a length between 0.3 and 1.0 mm. The distal triangular portion 16 will have a base of the same width as the rectangular sheet 15 and a height between 0.3 and 0.8 mm. The edges will be sharp to facilitate the insertion.

Part B:

The part B has the form of a rectangular sheet that punctures the corneal limbus 4 and stays in this place, being located between the cornea 1 and sclera 2. The upper surface of the device in contact with the cornea 1 and the lower surface in contact with the sclera 2, allow the draining of aqueous humor from the anterior chamber 8 to an intrascleral 2 or episcleral 13 space. The sheet of the part B is continued in its forward end with the part A, of the same width, and on the back end with the part C, which it is wider to prevent the device from penetrating beyond the length of the part B.

The part B punctures the corneal limbus 4 and stays in this place located between the cornea 1 and sclera 2. The upper surface of the device in contact with the cornea 1 and the lower surface in contact with the sclera 2, will allow the drainage of the aqueous humor from the anterior chamber 8 to an intrascleral 2 or episcleral 13 space. The part B is continued in its forward end with the part A and on the back end with the part C.

The upper surface of the part B is in contact with the cornea 1 and forms with it a space through which the aqueous humor will flow. The bottom surface is in contact with the sclera 2 and forms another space through which the aqueous humor will drain. The surfaces of this sheet are smooth, rough, wavy, corrugated or other finish. The part B of the device has a length between 0.3 and 1.2 mm; a width equal to that of the portion A, that is between 0.5 and 4 mm; and a thickness between 0.02 and 0.3 mm.

Part C:

The part C has a length between 0.5 and 15 mm, a width between 0.7 and 5 mm and a thickness between 0.02 and 0.3 mm; it is thin, malleable and is curved to the eye curvature.

The part C, which has the form of a rectangular sheet with rounded edges, it is wider than the part B. This sheet may be smooth, rough, wavy, corrugated or other finish, will be outside of the eye covered by the scleral flap 9, will go through the scleral space 2, episcleral space 13 or both.

It is in the corneal limbus area 4, where the flap 9 will be made to create the space to insert the device. This flap will be similar to those obtained for a trabeculectomy surgery and will have about 4 mm of length, 4 mm of width and a depth of about 50% of the scleral thickness.

The part C of the device is longer and apart from being located between the scleral flap 9 and the sclera 2, goes out towards the episcleral space 13, creating a corridor that leads to the ocular equator increasing the area of diffusion of the aqueous humor. This can be very beneficial in neovascular glaucoma.

The surgical procedure needed to insert the device includes all or some of the following steps:

a. An incision is made in the conjunctiva that may be limbus or fornix based, b. A scleral flap of approximately 4×4 mm is delimited with a depth of approximately 50% of the scleral thickness and a dissection parallel to the sclera is made until entering 1 mm into the corneal tissue, c. Paracentesis is performed parallel to the iris in the corneal limbus with a sharp blade of 15°, d. The device is inserted into the paracentesis, e. The flap is closed with 2 loose stiches, f. The conjunctiva is closed.

It will be understood that the foregoing description is of preferred exemplary embodiments of the invention and that the invention is not limited to the specific forms shown or described herein. Various modifications may be made in the design, arrangement, and type of elements disclosed herein, as well as the steps of making and using the invention without departing from the scope of the invention as expressed in the appended claims.

The invention claimed is:

1. A flat one-piece device for drainage of an aqueous humor of an eye, comprising three parts:
   a first part for use in the anterior chamber of the eye,
   a second part for use in connecting the anterior chamber with the exterior of the eye, and a third part located outside of the eye,
   wherein the device is a flat sheet nonadherable to ocular tissues surrounding said device; the second part consisting of a flat sheet form nonadherable to the ocular tissues and is for use in an incision made in the corneal limbus, under a scleral flap or conjunctivalflap, between the cornea and sclera; the device being responsive to a change of intraocular pressure so that the device is configured to create a space between the ocular tissues and the device to relieve an increase of intraocular pressure and the space is closed when the intraocular pressure is decreased.

2. The flat one-piece device for drainage of the aqueous humor of the eye, according to claim 1, characterized in that the device is made of a material selected from the group consisting of stainless steel, gold, platinum, silicone, nickel, molybdenum, metal alloys and ceramics.

3. The flat one-piece device for drainage of the aqueous humor of the eye, according to claim 1, characterized in that the first part has a width between 0.5 and 4 and has sharp edges to facilitate its insertion.

4. The flat one-piece device for drainage of the aqueous humor of the eye, according to claim 1, characterized in that the second part has a length between 0.3 and 1.2 mm; a width between 0.5 and 4 mm; and a thickness between 0.02 and 0.3 mm.

5. The flat one-piece device for drainage of the aqueous humor of the eye, according to claim 1, characterized in that the third part is for use in an intrascleral space of the eye an episcleral space or in both.

6. The flat one-piece device for drainage of the aqueous humor of the eye, according to claims 1 and 5, characterized in that the third part has a length between 0.5 and 15 mm, a width between 0.7 and 5 mm and a thickness between 0.02 and 0.3 mm.

7. The flat one piece device drainage of the aqueous humor of the eye according to claim 1, wherein thea flat sheet is malleable and creates the space between the flat sheet and the ocular tissues on the increase of intraocular pressure.

* * * * *